United States Patent [19]

Williamson

[11] 4,202,837

[45] May 13, 1980

[54] CONVERSION OF UNSATURATED ALDEHYDES TO UNSATURATED NITRILES

[75] Inventor: Alex N. Williamson, Greensboro, N.C.

[73] Assignee: Monsanto Company, St. Louis, Mo.

[21] Appl. No.: 961,177

[22] Filed: Nov. 16, 1978

[51] Int. Cl.$^2$ ............................................ C07C 120/00
[52] U.S. Cl. .................................. 260/465.9; 260/464; 260/465 D; 260/465 F; 260/465 G; 260/465 K; 260/465.4; 260/465.6; 260/465.7; 260/940
[58] Field of Search ................ 260/465.9, 465 K, 464

[56] References Cited

U.S. PATENT DOCUMENTS

| | | | |
|---|---|---|---|
| 2,691,037 | 10/1954 | Bellringer et al. | 260/465.9 |
| 3,719,701 | 3/1973 | Bach | 260/465.9 |
| 3,940,429 | 2/1976 | McConaghy, Jr. et al. | 260/465.9 |

OTHER PUBLICATIONS

Brackman, et al., Recueil, 82, (1963), pp. 757–762.
Misono, et al., Bull. Chem. Soc. of Japan, 40, (1967), pp. 912–919.

Primary Examiner—Joseph Paul Brust
Attorney, Agent, or Firm—J. C. Bolding

[57] ABSTRACT

Conversion of an unsaturated aldehyde to an unsaturated nitrile having the same number of carbon atoms is carried out in the presence of a catalyst complex formed by addition of $NH_3$ to a copper salt.

7 Claims, No Drawings

CONVERSION OF UNSATURATED ALDEHYDES TO UNSATURATED NITRILES

BACKGROUND OF THE INVENTION

Polymers derived from unsaturated nitrile monomers, such as acrylonitrile, methacrylonitrile, vinylidene cyanide, etc., are well known in the art. Of this class of monomers, acrylonitrile is presently the most important and is used in making a variety of commercial products, e.g., butadiene-acrylonitrile copolymer rubbers and acrylic textile fibers.

Acrylonitrile has been manufactured by a two-stage process wherein ethylene oxide and hydrogen cyanide are reacted to form ethylene cyanohydrin which is subsequently subjected to dehydration. It has also been manufactured by the direct reaction of acetylene and hydrogen cyanide. However, this latter method of manufacture has not proven promising due to the formation of by-products and the difficulties encountered in separating the acrylonitrile from the by-products, for example, the acrylonitrile tends to polymerize during the multistage stripping and distillation procedures.

There is a large interest in manufacturing acrylonitrile from ammonia and hydrocarbons. One such process involves the catalytic amination of propylene at high temperatures and pressures to form propionitrile, which is then dehydrogenated. Another process involves the reaction of propylene, ammonia and oxygen at high temperatures to form acrylonitrile directly. Although potentially less expensive, the direct methods have the disadvantages of troublesome by-products and requiring expensive equipment.

Another route to unsaturated nitriles is disclosed in U.S. Pat. No. 2,691,037. This patent teaches a process for preparing unsaturated nitriles from unsaturated aldehydes in the vapor phase, in which the aldehyde is reacted with ammonia and molecular oxygen at elevated temperatures in the presence of a metal or metal oxide catalyst such as, e.g., copper.

A liquid phase, low temperature route to aromatic nitriles from aromatic aldehydes is reported in RECUEIL, v. 82, pp. 757–762 (1963). In this process, a copper-ammonia complex catalyst and a strong base are employed in a methanol solution. However, this process proved unsuccessful when applied to an unsaturated aldehyde, namely acrolein, only a "trace" of acrylonitrile being produced. More recently, benzaldehyde ammoxidation to benzonitrile was reported in Bulletin of the Chemical Society of Japan, v. 40, pp. 912–919 (1967), using a liquid phase process in a methanol solvent, and employing various copper salts as a catalyst.

While such liquid phase, copper catalyzed processes have proven successful for preparation of saturated or aromatic nitriles, the high reactivity of the olefinic double bond of unsaturated nitriles such as acrylonitrile, methacrylonitrile, and the like has prohibited the use of such processes to produce these compounds. For ammoxidation of the highly reactive unsaturated aldehydes, it is necessary to keep the level of free ammonia quite low in order that the unsaturated aldehyde does not undergo an ammonia catalyzed polymerization such as is reported by C. W. Smith in his book "Acrolein", John Wiley & Sons, New York (1962) at pp. 13–15; in accordance with the present invention this may be done by employing a copper-ammonia complex catalyst which serves both as the catalyst and as the source of ammonia for the ammoxidation reaction. The copper-ammonia complex may advantageously be preformed prior to addition of the unsaturated aldehyde to be ammoxidized; alternatively, the complex may be formed during the ammoxidation by slow, controlled addition of ammonia to the reaction mixture.

Accordingly, it is an object of this invention to provide a simple, economic liquid phase process for the production of olefinically unsaturated nitriles.

It is also an object of this invention to provide a process for the preparation of unsaturated nitriles from corresponding unsaturated aldehydes in high yields and substantially free of undesirable by-products.

Other objects and advantages of the invention will become apparent from the following detailed description.

SUMMARY OF THE INVENTION

The process of the present invention is one for the conversion of an unsaturated aldehyde to an unsaturated nitrile which comprises contacting an unsaturated aldehyde in the preence of molecular oxygen with a solution containing a complex formed by addition of ammonia ($NH_3$) to a copper salt, at a temperature of from 0° to 200° C. and an oxygen partial pressure of from 0.1 to 10 $kg/cm^2$.

The unsaturated aldehyde used in the process of this invention is of the formula

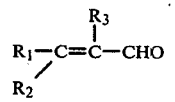

wherein $R_1$, $R_2$ and $R_3$ represent hydrogen or monovalent organic radicals. Suitable monovalent organic radicals include alkyl, olefinically unsaturated aliphatic, cycloaliphatic, alkaryl, aromatic, heteroaromatic and halogenated hydrocarbon radicals (e.g., chlorinated and brominated hydrocarbon radicals) and radicals of the formula

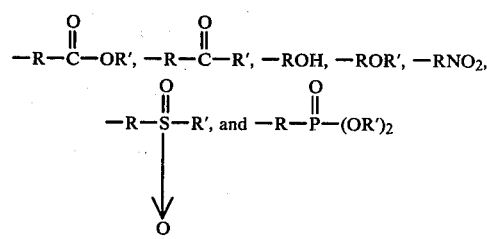

wherein R represents a divalent hydrocarbon radical, such as alkylene or phenylene and R' represents a monovalent hydrocarbon radical such as an alkyl or phenyl, Representative monovalent radicals include:

—$CH_3$,  —$CH_2CH_2Cl$,
—$C_2H_5$,  —$CCl_2CCl_2CCl_3$,
—$CH_2CH(CH_3)CH_3$

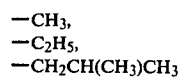
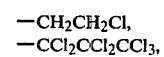

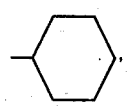
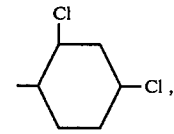

-continued

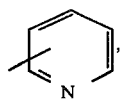   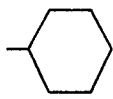

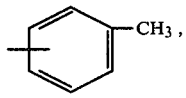   —CH$_2$CH$_2$Br
—CH$_2$CH$_2$OCH$_2$CH$_3$,

—CH$_2$—C(=O)—O—CH$_2$CH$_3$,   —CH$_2$C(=O)—CH$_3$,
—CH$_2$CH$_2$CH$_2$NO$_2$,

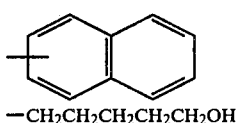

—CH$_2$CH$_2$CH$_2$CH$_2$CH$_2$OH,

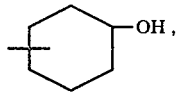   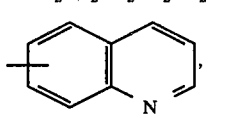

and the like.

The unsaturated aldehyde employed in the reaction may be prepared by well known procedures described in the literature, such as by the catalytic oxidation of an olefin hydrocarbon. One such procedure is described in Example 13 of U.S. Pat. No. 3,816,596, in which propylene is oxidized over an antimony-uranium catalyst to produce acrolein. Another procedure is set forth in Tables 3 and 4 of U.S. Pat. No. 3,688,147 wherein propylene and isobutylene are oxidized, respectively, over a promoted iron oxide-antimony oxide catalyst to yield acrolein and methacrolein.

Generally, the unsaturated aldehydes used in carrying out the process of the invention contain from 3 to 24 carbon atoms. Typical examples of such unsaturated aldehydes and the corresponding unsaturated nitriles prepared therefrom by the process of the invention are:

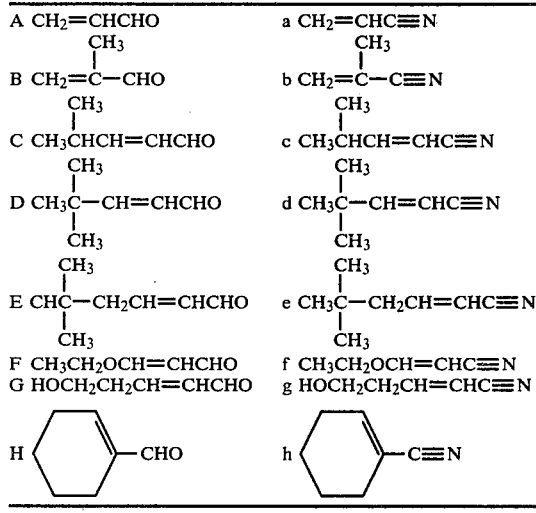

The aldehyde reactant may consist of one aldehyde or a mixture of aldehydes. For example, methacrylonitrile and acrylonitrile may be prepared simultaneously by the process described herein by using, as the reactant, a mixture of methacrolein and acrolein.

In carrying out the process defined herein the unsaturated aldehyde reactant must not contain substituent groups which either are oxidizable or inactivate the catalyst under the process conditions. In this context oxidizable groups are primary or secondary amine groups, and groups which inactivate the catalyst are acid groups, such as carboxy and sulfonic acid groups.

A variety of solvents may be employed in the liquid phase reaction. Suitable solvents include pyridine, n-methyl pyrrolidone, sulfolane, alcohols, aromatic hydrocarbons, and others. The nature of the solvent is not critical, so long as it will dissolve a sufficient amount of the copper salt-ammonia catalyst complex. Pyridine and n-methyl pyrrolidone are preferred solvents.

The catalyst comprises a copper salt-ammonia complex. While the nature of this complex is not fully understood, it is believed that oxygen is also a component of the catalyst complex. A variety of copper salts may be employed in the preparation of the catalyst complex. Suitable salts, by way of example, include CuCl, CuBr, Cu(OH)$_2$, cuprous acetate, cupric acetate, cuprous nitrate, The proportions of the components of the catalyst complex of copper salt and ammonia can vary widely but in general the molar ratio of copper salt to ammonia can be from 1:10 to 10:1 and preferably from about 1:1 to 1:5.

The process can be operated at atmospheric or superatmospheric pressures and pressures of 0.1 kg/cm$^2$ to 10 kg/cm$^2$ are preferred.

The temperature at which the reaction is conducted can be from 0° C. to 200° C. but in general temperatures of from 25° C. to 100° C. are preferred.

The catalyst can conveniently be prepared by adding the copper salt to the solvent with stirring, then treating with oxygen until oxygen uptake ceases, then adding HN$_3$.

In a preferred mode of operation, molecular oxygen is used as the primary oxidant and may be introduced into the reaction medium by diffusion or injection techniques. Pure oxygen may be used, or alternatively, air or other gases containing free oxygen may be used as the oxidant. To obtain optimum yields of the desired nitrile products, a molar ratio of oxygen to aldehyde of at least one is used and, preferably, a molar excess of oxygen to aldehyde is used. However, higher or lower ratios may be used, if desired, since unreacted aldehyde can be recovered and the yield of nitrile is substantially unaffected by using an excess of aldehyde or oxygen. Likewise, it is preferred to use a molar ratio of NH$_3$ to aldehyde of at least one, and more preferably a molar excess of NH$_3$ is employed to improve yields of the nitrile.

When the batch process is used, the catalyst system may be prepared as indicated above, preferably at room temperature, and the unsaturated aldehyde is added thereto under an atmosphere of oxygen and ammonia with stirring for a period of time sufficient to ensure complete reaction. In this respect, a gas chromatograph has been found to be an excellent means for following the progress of the reaction. After completion, the nitrile product may be separated from the reaction mixture by distillation and the reaction repeated after reactivation of the catalyst by treatment with oxygen and ammonia.

When the continuous process is used, it is preferable that the copper salt/ammonia complex be prepared (with or without an inert solvent) and the unsaturated aldehyde be added thereto. In such a process the aldehyde is conveniently added at a slow rate to the reaction mixture while simultaneously passing a stream of air, other oxidant gas mixture or molecular oxygen and ammonia through the solution at a temperature and flow rate such that optimum reaction conditions are established with respect to nitrile product formation and the removal thereof from the reaction mixture by the gas sweep. The product is then removed from the exit gas stream by any well known method. The water formed as a result of the oxidation reaction may be removed from the nitrile by any suitable means such as by fractionation or the use of drying agents.

In actual operation, the optimum reaction conditions to be used in carrying out the process will depend on the reactants used, the oxidant selected, and whether the continuous or batch method is employed. The optimum conditions for a given specific reaction and method can be readily determined by a few preliminary experiments.

To further illustrate the invention, the following examples are given:

EXAMPLE I

This example illustrates the poor yields obtained when the reaction is carried out in the conventional manner; i.e., using free (uncomplexed) ammonia in a fashion similar to the process reported by Misono et al in Bulletin of the Chemical Society of Japan, v. 40, pp. 912–919 (1967). CuBr (2.9 g—20 mmoles) was dissolved in 100 ml of pyridine and stirred under $O_2$ pressure of 2.1 kg/cm$^2$ gauge for 30 minutes at 75° C. The $O_2$ was then partially vented and the vessel repressured to 30 psig with $HN_3$. To the vessel was added a solution of acrolein (1.12 g—10 mmoles) in 20 ml of pyridine and the contents were stirred for 2 hrs. Analysis by gas chromatography showed that all the acrolein had been consumed but no acrylonitrile was detected.

EXAMPLE II

This example according to the present invention illustrates the benefit of preforming the $NH_3$ catalyst complex.

A solution of cuprous bromide (2.91 g—20.3 mmoles) in pyridine (100 ml) was stirred under 1.76 kg/cm$^2$ gauge $O_2$ pressure (glass pressure vessel) for 1 hr. To this solution $NH_3$ was added at a rate of about 0.5 mmol min$^{-1}$ for two hours. A greenish-black precipitate formed. The reaction vessel was depressurized and the solution purged with $N_2$ for 15 minutes to remove any uncomplexed $NH_3$. The reaction vessel was then repressured to 1.76 kg/cm$^2$ gauge with $O_2$ and its contents treated with 50 ml of solution of acrolein (1.2 g—21.4 mmol) and n-heptane (internal standard for gas chromatographic analysis) in pyridine. The solution was added at a rate of 0.41 mmol min$^{-1}$ over a period of 52 minutes. Yield data were obtained after all the acrolein had been added.

TABLE 1

| Temperature (°C.) | AN Yield (%) |
|---|---|
| 50 | 19 |
| 75 | 29 |
| 110 | 13 |

EXAMPLE III

This example illustrates the effect of various solvents for the reaction mixture. Reactions were run as in Example II at 75° C., with the exception that other solvents were substituted for pyridine. The results are shown in Table 2.

TABLE 2

| Solvent | AN Yield (%) |
|---|---|
| N-methylpyrrolidone | 18 |
| n-hexanol | 2 |
| sulfolane | 7 |

EXAMPLE IV

This example illustrates the effect of the acrolein/CuBr ratio. Reactions were run as in Example II at 75° C. except the amount of acrolein added was varied to provide the ratios shown in Table 3.

TABLE 3

| Acrolein/CuBr Ratio | AN Yield (%) |
|---|---|
| 1.8 | 29 |
| 1.2 | 40 |

EXAMPLE V

This example illustrates the effectiveness of various copper salts on the reaction. All runs were as in Example II at 75° C., using other copper salts in place of CuBr, shown in Table 4.

TABLE 4

| Catalyst | AN Yield (%) |
|---|---|
| Cuprous chloride | 8 |
| Cupric acetate | 12 |

EXAMPLE VI

This example shows it is also possible to run the reaction with slow controlled addition of ammonia instead of performing a complex with copper salts. This technique is made possible because the ammonia reacts with the copper salt to form the complex much more rapidly than it reacts with the aldehyde to cause polymerization.

A solution of cuprous chloride (2.06 g—20 mmol) and n-heptane (0.9 g—8.9 mmol; internal standard for gas chromatographic analysis) in pyridine (100 ml) was stirred under 1.76 kg/cm$^2$ gauge $O_2$ pressure at 50° C. in a glass pressure bottle. Ammonia was added to the vessel at a rate of 0.41 mmol min$^{-1}$ for a period of 82 minutes. (30% excess of $NH_3$ had been added, showed 92% conversion of acrolein and an acrylonitrile yield of 27%. Cuprous bromide and cupric acetate were also effective catalysts under the conditions of slow $NH_3$ addition. Results obtained with these two salts are shown in Table 5. These reactions were conducted at 50° C. under the same conditions as set out above in this example.

TABLE 5

| Catalyst | AN Yield (%) |
|---|---|
| Cuprous bromide | 19 |
| Cuprous acetate | 15 |

It should be noted that in one attempt to ammoxidize acrolein employing the slow ammonia addition technique, the reaction was unsuccessful. While the reason for this lack of success is unknown, it is believed that the solution was allowed to become too basic, resulting in polymerization of the acrolein.

I claim:

1. A process for ammoxidation of an olefinically unsaturated aldehyde selected from acrolein and methacrolein to the corresponding unsaturated nitrile in the liquid phase comprising the steps of
   (a) forming a complex of a copper salt with ammonia wherein the molar ratio of copper salt to ammonia is from 1:10 to 10:1 in a solvent by contacting said copper salt with ammonia, and
   (b) contacting the complex with the unsaturated aldehyde in the presence of molecular oxygen in the substantial absence of free ammonia.

2. The process of claim 1 wherein the solvent is selected from pyridine and n-methylpyrrolidone.

3. The process of claim 1 wherein the reaction temperature is maintained in the range of 0° to 200° C.

4. The process of claim 1 wherein the oxygen partial pressure is between 0.1 and 10 kg/cm$^2$.

5. The process of claim 1 wherein the molar ratio of copper salt to ammonia is from 1:1 to 1:5.

6. The process of claim 1 wherein the complex is preformed prior to contacting with the unsaturated aldehyde.

7. The process of claim 1 wherein the complex is formed in the presence of the unsaturated aldehyde by slow addition of ammonia.

* * * * *